US012599732B2

(12) United States Patent
Sandiford

(10) Patent No.: US 12,599,732 B2
(45) Date of Patent: Apr. 14, 2026

(54) VARIABLE CAMSHAFT

(71) Applicant: ITT Manufacturing Enterprises LLC, Wilmington, DE (US)

(72) Inventor: A. David Sandiford, Valencia, CA (US)

(73) Assignee: ITT Manufacturing Enterprises LLC, Stamford, CT (US)

( * ) Notice: Subject to any disclaimer, the term of this patent is extended or adjusted under 35 U.S.C. 154(b) by 810 days.

(21) Appl. No.: 17/922,305

(22) PCT Filed: Jun. 1, 2021

(86) PCT No.: PCT/US2021/035101
§ 371 (c)(1),
(2) Date: Oct. 28, 2022

(87) PCT Pub. No.: WO2021/252221
PCT Pub. Date: Dec. 16, 2021

(65) Prior Publication Data
US 2023/0201500 A1      Jun. 29, 2023

Related U.S. Application Data

(60) Provisional application No. 63/037,091, filed on Jun. 10, 2020.

(51) Int. Cl.
*A61M 16/00*      (2006.01)
*F16H 53/04*      (2006.01)

(52) U.S. Cl.
CPC ......... *A61M 16/0084* (2014.02); *F16H 53/04* (2013.01); *A61M 2205/10* (2013.01); *A61M 2205/8262* (2013.01)

(58) Field of Classification Search
CPC .............. A61M 16/00; A61M 16/0045; A61M 16/0057–0084; A61M 16/20–209;
(Continued)

(56) References Cited

U.S. PATENT DOCUMENTS

| | | | |
|---|---|---|---|
| 2008/0023925 A1 | 1/2008 | Tomita et al. | |
| 2011/0000450 A1* | 1/2011 | Shiino | F01L 1/344 123/90.17 |
| 2017/0197047 A1* | 7/2017 | Minato | A61M 16/0078 |

FOREIGN PATENT DOCUMENTS

| | | |
|---|---|---|
| KR | 102067085 B | 1/2020 |
| KR | 102263654 B | 6/2021 |

OTHER PUBLICATIONS

International Search Report and Written Opinion for International App No. PCT/US21/35101, pp. 9.

* cited by examiner

*Primary Examiner* — Rachel T Sippel
*Assistant Examiner* — Jacqueline M Pinderski
(74) *Attorney, Agent, or Firm* — Turk IP Law, LLC

(57) ABSTRACT
A one or more plane, variable camshaft is described. The single plane camshaft includes a circular drive plate with two radial drive slots on opposing sides of the center, four arms movably coupled at respective endpoints and arranged in a polar configuration, and a scroll plate to allow adjustable operation of the camshaft. Multiple plane camshafts may include a number of half drive plates arranged around a drive block and secured to a base washer through a scroll block. The variable camshaft may be incorporated into portable, motorized or manual, bag valve mask based resuscitation devices or similar ones.

12 Claims, 10 Drawing Sheets

100

(58)  Field of Classification Search
    CPC ...... A61M 2205/10; A61M 2205/8262; A61M
        2205/8206; F16H 25/06; F16H 53/00–08
    See application file for complete search history.

VARIABLE CAMSHAFT

CROSS-REFERENCE TO RELATED APPLICATIONS

This application is a U.S. National Stage filing under 35 U.S.C. § 371 of International Application PCT/US21/35101, filed Jun. 1, 2021, which claims the benefit of U.S. Provisional Patent Application Ser. No. 63/037,091 filed on Jun. 10, 2020. The disclosures of the above application are hereby incorporated by reference for all purposes.

BACKGROUND

Unless otherwise indicated herein, the materials described in this section are not prior art to the claims in this application and are not admitted as prior art by inclusion in this section.

Control of maximal air volume (tidal volume) during Bag Valve Mask (BVM) resuscitation is critical in controlling a variety of complications including hyperventilation, hypoxia, aspirational pneumonia or barotrauma as well as other issues. A high level of concentration is required to continuously provide a consistent cycle of breaths for extended periods of time, as during transportation to a hospital. In order for a mechanical resuscitator assist device to address these issues, a methodology must be utilized that allows volume variation without a long delay for adjustment that could be detrimental to the patient.

SUMMARY

The present disclosure generally describes a one or more plane, variable camshaft for use in portable, motorized or manual, bag valve mask based resuscitation devices or similar ones.

According to some examples, a single plane variable camshaft may include a drive plate comprising a first substantially circular plate member, a center shaft member protruding from a center of the first circular plate member, where the first circular plate member defines two radial drive slots on opposing sides of the center shaft member; four arms movably coupled at respective endpoints and arranged in a polar configuration; four roller extensions coupled to respective end points of two pairs of the arms, where one pair of the roller extensions are arranged to fit into respective radial drive slots; and a scroll plate comprising a second substantially circular plate member. The second substantially circular plate member defines a substantially circular center hole to fit around the center shaft member and two "S" shaped scroll slots on opposing sides of the center hole, and another pair of the roller extensions are arranged to fit into respective scroll slots.

According to further examples, a dual plane variable camshaft may include a base washer; a drive block aligned centrally with the base washer; a first half drive camshaft comprising a first camshaft member and a first stud that protrudes transversally from the first camshaft member, where the first camshaft member defines a substantially centrally located first opening to fit around the drive block; a second half drive camshaft comprising a second camshaft member and a second stud that protrudes transversally from the second camshaft member, where the second camshaft member defines a substantially centrally located second opening to fit around the drive block and a third opening to fit around the first stud; a substantially circular scroll block that defines a substantially circular center hole to fit around a threaded top portion of the drive block and two "S" shaped scroll slots on opposing sides of the center hole; a fastening mechanism to secure the transversally ordered base washer, drive block, first half drive camshaft, second half drive camshaft, and scroll block together, where the fastening mechanism is arranged to thread to the threaded top portion of the drive block; and a cover plate to fit into a substantially circular opening at a top surface of the scroll block.

According to other examples, a bag mask valve (BMV) based resuscitator may include an inflatable bag arranged to provide air to a patient through a face mask or an endotracheal tube in response to compression/retraction actions applied to the inflatable bag; a motor; a pair of levers positioned to surround a central portion of the inflatable bag and arranged to provide the compression/retraction actions to the inflatable bag in response to a rotational motion from the motor; and a camshaft mechanically coupled between the motor and the pair of levers. The camshaft may include a drive plate comprising a first substantially circular plate member, a center shaft member protruding from a center of the first circular plate member, where the first circular plate member defines two radial drive slots on opposing sides of the center shaft member; four arms movably coupled at respective endpoints and arranged in a polar configuration; four roller extensions coupled to respective end points of two pairs of the arms, where one pair of the roller extensions are arranged to fit into respective radial drive slots; and a scroll plate comprising a second substantially circular plate member. The second substantially circular plate member defines a substantially circular center hole to fit around the center shaft member and two "S" shaped scroll slots on opposing sides of the center hole, and another pair of the roller extensions are arranged to fit into respective scroll slots.

According to further examples, a bag mask valve (BMV) based resuscitator may include an inflatable bag arranged to provide air to a patient through a face mask or an endotracheal tube in response to compression/retraction actions applied to the inflatable bag; a motor; a pair of levers positioned to surround a central portion of the inflatable bag and arranged to provide the compression/retraction actions to the inflatable bag in response to a rotational motion from the motor; and a camshaft mechanically coupled between the motor and the pair of levers. The camshaft may include a base washer; a drive block aligned centrally with the base washer; a first half drive camshaft comprising a first camshaft member and a first stud that protrudes transversally from the first camshaft member, where the first camshaft member defines a substantially centrally located first opening to fit around the drive block; a second half drive camshaft comprising a second camshaft member and a second stud that protrudes transversally from the second camshaft member, where the second camshaft member defines a substantially centrally located second opening to fit around the drive block and a third opening to fit around the first stud; a substantially circular scroll block that defines a substantially circular center hole to fit around a threaded top portion of the drive block and two "S" shaped scroll slots on opposing sides of the center hole; a fastening mechanism to secure the transversally ordered base washer, drive block, first half drive camshaft, second half drive camshaft, and scroll block together, where the fastening mechanism is arranged to thread to the threaded top portion of the drive block; and a cover plate to fit into a substantially circular opening at a top surface of the scroll block.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

Figures 5A, 5B, 5C, 5D, 5E:
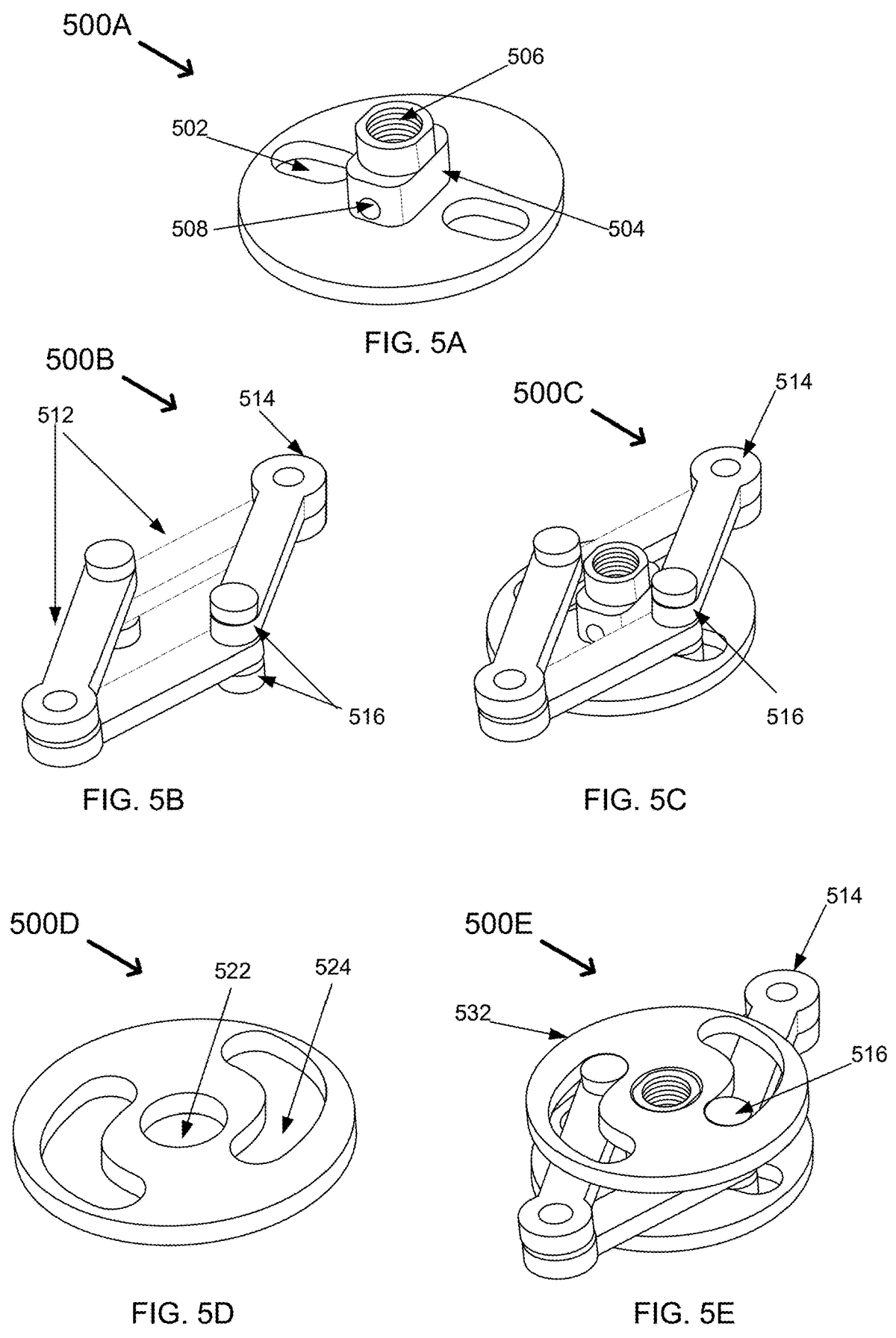

FIG. 5A through 5F illustrate various perspective views of individual components and partially assembled single plate cams;

DETAILED DESCRIPTION

Figure 1:
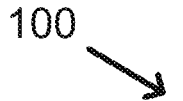
FIG. 1 illustrates a side view of an example portable respirator with a variable cam.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. The aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to methods, apparatus, systems and/or devices related to one or more plane, variable camshaft for use in portable, motorized or manual, bag valve mask based resuscitation devices or similar ones.

A camshaft (also referred to as "cam") is a relatively basic component to convert rotational motion to linear motion and includes shaped lobes called cams. When the camshaft is rotated, the shape of the cams allows it to act upon a valve or switch, for example, to a degree matching the severity of its shape with the speed of rotation controlling the rate of action. While a camshaft is widely used in automobile engines and similar applications, its applicability can be fairly wide.

A bag valve mask, also known by the proprietary name Ambu bag® or generically as a manual resuscitator or self-inflating bag, is a hand-held device commonly used to provide positive pressure ventilation to patients who are not breathing or not breathing adequately. The device is used in out-of-hospital settings (such as ambulance crews) and in hospitals as part of standard equipment found on a crash cart, in emergency rooms or other critical care settings. Manual resuscitators are also used for temporary ventilation of patients. The bag valve mask includes a flexible air chamber (the bag), attached to a face mask via a shutter valve. When the face mask is properly applied and the bag is squeezed, the device forces air through into the patient's lungs; when the bag is released, it self-inflates from its other end, drawing in either ambient air or a low pressure oxygen flow supplied by a regulated cylinder, while also allowing the patient's lungs to deflate to the ambient environment (not the bag) past the one way valve.

An example variable camshaft may be incorporated into a BVM based resuscitator, which may be motorized or manually operated. A BVM based resuscitator involves simple and reliable mechanical operation without multiple controls that may require special training. Simple and smooth enclosure may allow preservation of sterility and quick disinfection. Levers sandwiched between two parts of the enclosure and controlled by a cam provide compression and retraction of an inflatable bag. With the levers hidden inside the enclosure, catching of hazards (e.g., entangling with tubes) or damage to the levers during operation can be avoided. With a handgrip and a removable, keyed stand, the device may be used in-hand (a healthcare professional holding the device over the mouth of a patient) or affixed to a crash cart or other location (connected to the mask or endotracheal tube through tubing) as shown in FIG. 1. A variable camshaft as discussed herein may be implemented in a single plane configuration, dual-plane configuration, or multiple plane configuration. Furthermore, embodiments are not limited to resuscitation devices incorporating a variable camshaft. Any mechanical system utilizing rotational-linear motion conversion may be implemented with a variable camshaft as described herein.

FIG. 1 illustrates a side view of an example portable respirator with a variable cam, arranged in accordance with at least some embodiments described herein.

The BVM based resuscitator in FIG. 1 includes an inflatable bag 104, mask 106, enclosure 102, and variable camshaft 110 incorporated into the enclosure 102. The enclosure 102 surrounds the inflatable bag 104 and includes levers that compress and relax the bag allowing air (or pure oxygen) to be delivered to a patient through the mask 106.

In some examples, a direct current (DC) motor may be used to move the cam/lever structure. High reliability of the DC motor and connectivity to an external power source may allow easy transition between environments (e.g., from ambulance to hospital, etc.) and reliable power supply (battery pack, vehicle power system, alternative current (AC) converters, etc.). In some examples, the inflatable bag may be replaceable by pushing the bag through the substantially circular aperture of the enclosure to install or to remove.

The inflatable bag, which may be made from an elastic material (PVC, polyurethane, etc.) may be inserted into the substantially circular aperture of the portable respirator's enclosure. The inflatable bag may be held in place by pressure or may include a pair of ridges around its equatorial region to prevent sliding out in either direction. One side of the inflatable bag may be attached to a face mask or endotracheal tube to provide air to the patient. The face mask or endotracheal tube may be attached to the bag through solid tubing or soft tubing material (e.g., in scenarios, where the respirator is affixed to a crash cart or similar fixed location). The connection to the face mask of endotracheal tube may be removable to allow replacement of the mask and/or bag. For example, different sizes (e.g., pediatric, adult) of masks may be used by simply connecting them to the inflatable bag tubing. The other side of the inflatable bag may include an opening to provide air from the environment or connection(s) to provide various concentrations of oxygen from an external oxygen supply (e.g., a tank, a building oxygen distribution system, etc.).

In some examples, the cam/lever system may perform two cycles of retraction/compression per revolution. The average respiration rate for an adult is in a range of 12 to 20 breaths per minute, whereas in infants, the rate may go up to 40 breaths per minute. A potentiometer coupled to the motor may be used to adjust the breath rate (retraction/compression cycles) manually (e.g., through a turn-knob, a slide control, etc.). In a normal breath, 500 and 800 milliliters of air may be needed by an adult. The volume of air may be reduced to 400 milliliters or even less if supplemental oxygen is used. Thus, a size of the inflatable bag may vary for adults and children (or even large adults and small adults). In some examples, the portable respirator enclosure (and the cam/lever system) may be made in different sizes to accommodate different sizes of inflatable bags. In other examples, the portable respirator enclosure (and the cam/lever system) may be adjustable for different diameters of inflatable bags.

Figure 2:
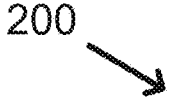
FIG. 2 illustrates a perspective view of a mechanically adjustable single plane variable cam in fully extended orientation.
Figure 2:
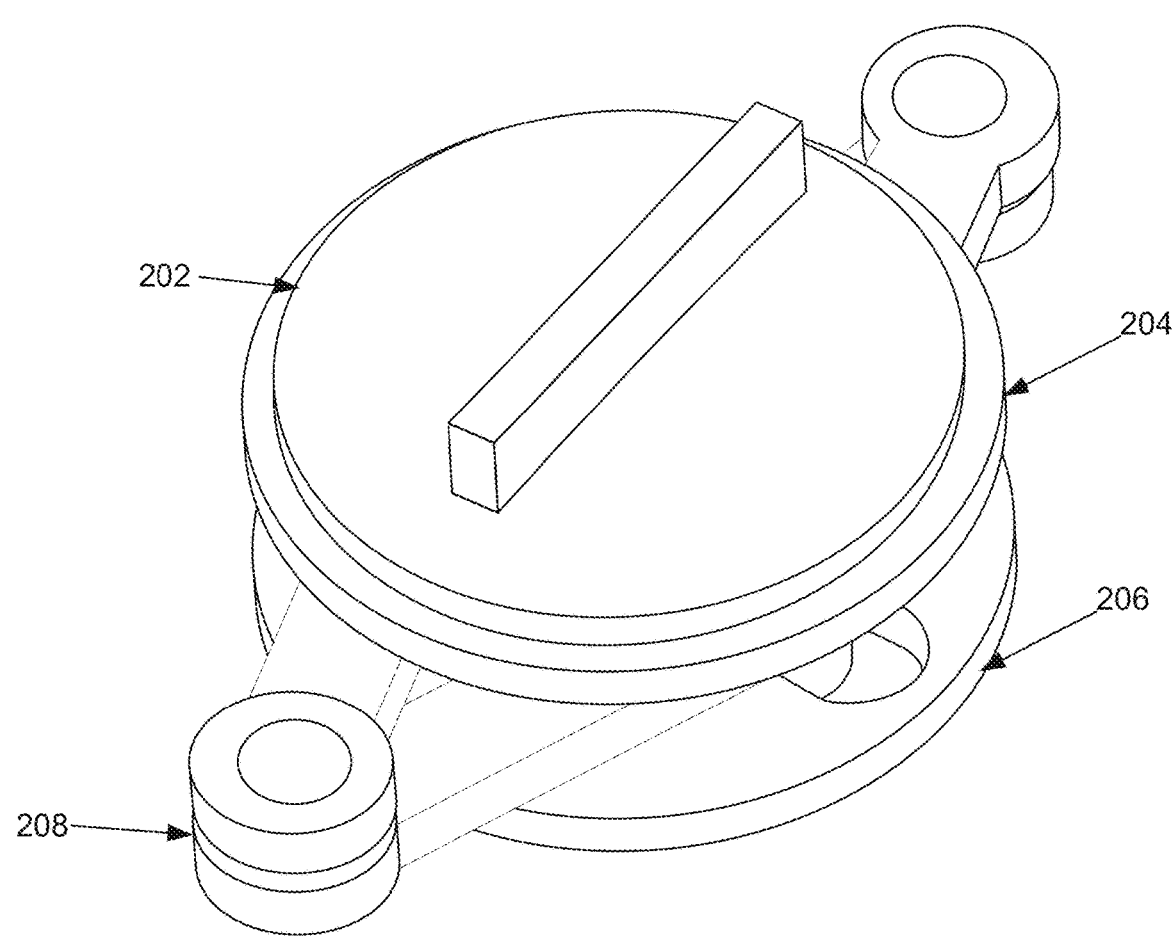

FIG. 2 illustrates a perspective view of a mechanically adjustable single plane variable cam in fully extended orientation, arranged in accordance with at least some embodiments described herein.

Diagram 200 shows a variable cam, where the arms 208 are sandwiched between a scroll plate 204 and drive plate 206. The cam assembly also includes a lock cover 202 to lock the assembly in place.

For a resuscitator assist device that operates from a rotation motor which transfers its leverage to a cam and thereby compressing "arms" (levers), the size (from tip to tip) of the cam determines the amount of deflection afforded to the bag. The more a BVM bag is depressed, the more air is generated. By varying the length of the cam, the volume of air delivered on any cycle can be determined.

Figure 3:
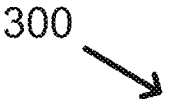
FIG. 3 illustrates a cross-section view of an example variable cam location in a resuscitator assist device.
Figure 3:
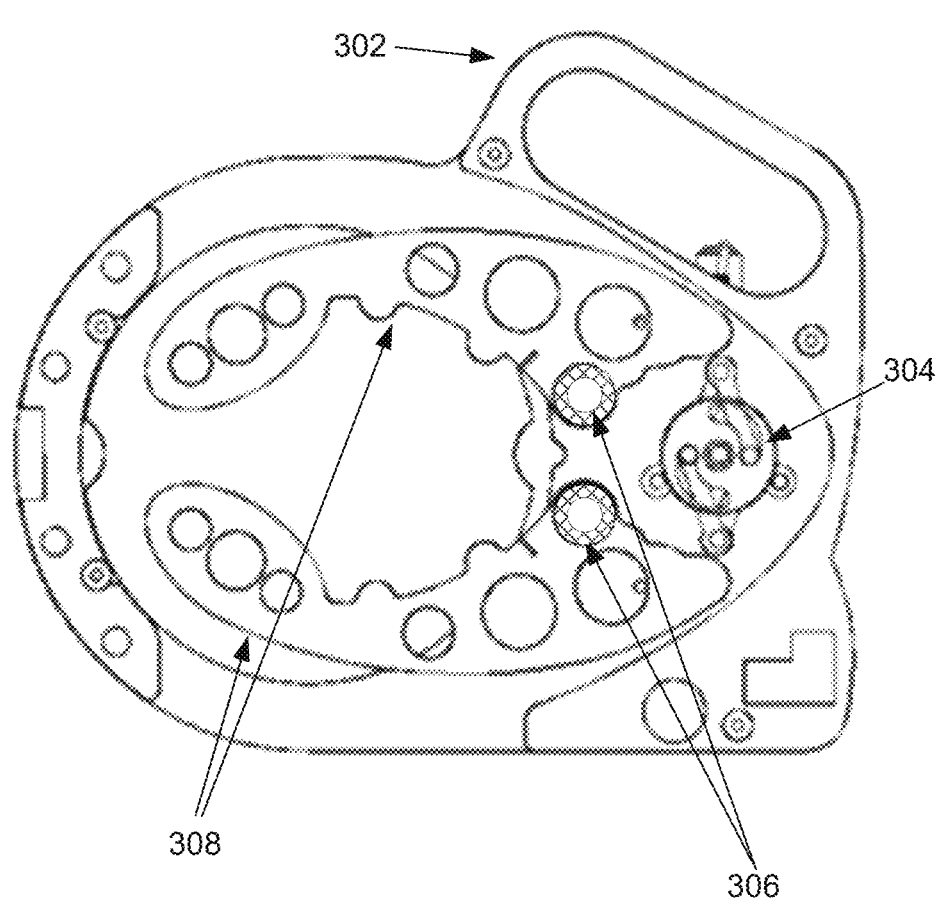

FIG. 3 illustrates a cross-section view of an example variable cam location in a resuscitator assist device, arranged in accordance with at least some embodiments described herein.

Diagram 300 shows a cross-section of the enclosure 102 of FIG. 1 with handle 302, compression arms (levers) 308, pivots (fulcrums) 306, and variable cam 304 acting as an adjustable effort to a Class 1 lever by rotation along the center axis.

The cam 304 and the levers 308 are sandwiched between two covers of the enclosure and their shapes and mechanical coupling may prevent them from separating or otherwise getting disassembled in either retracted or compressed states, as well as, when the inflatable bag is removed. The levers 308 and protrusions on the levers may be shaped such that in a compressed state, one hemisphere of the inflatable bag is collapsed simulating manual compression of the bag.

The cam 304, levers 308, and/or the covers of the enclosure may be made from various synthetic materials such as PVC, polypropylene, ceramic, or metals such as aluminum, stainless steel, and other materials. In one example implementation, the enclosure of the portable respirator may have a depth (distance between the surfaces of the two covers) of about 1.25 inches and the overall respirator may be about 11 inches wide and about 17 inches long. The keyed standup feet may be removable to allow even easier use in the manual mode and may include a number of predrilled holes to allow affixing of the respirator to fixed locations.

In addition to determining a volume of air delivered on any cycle by varying the length of the cam 304, a secondary consideration may be the necessary rotational speed of the motor. Electrical motors have an efficient range of rotational speed. Below this speed the motor can be damaged by heat or fail to generate sufficient torque to power the compressing "arms" through a resuscitator compression cycle. The variable cam shown in FIGS. 2 and 3 has a symmetrical cam shape, and therefore actuates the compressor arms twice per motor shaft revolution.

Figure 4:
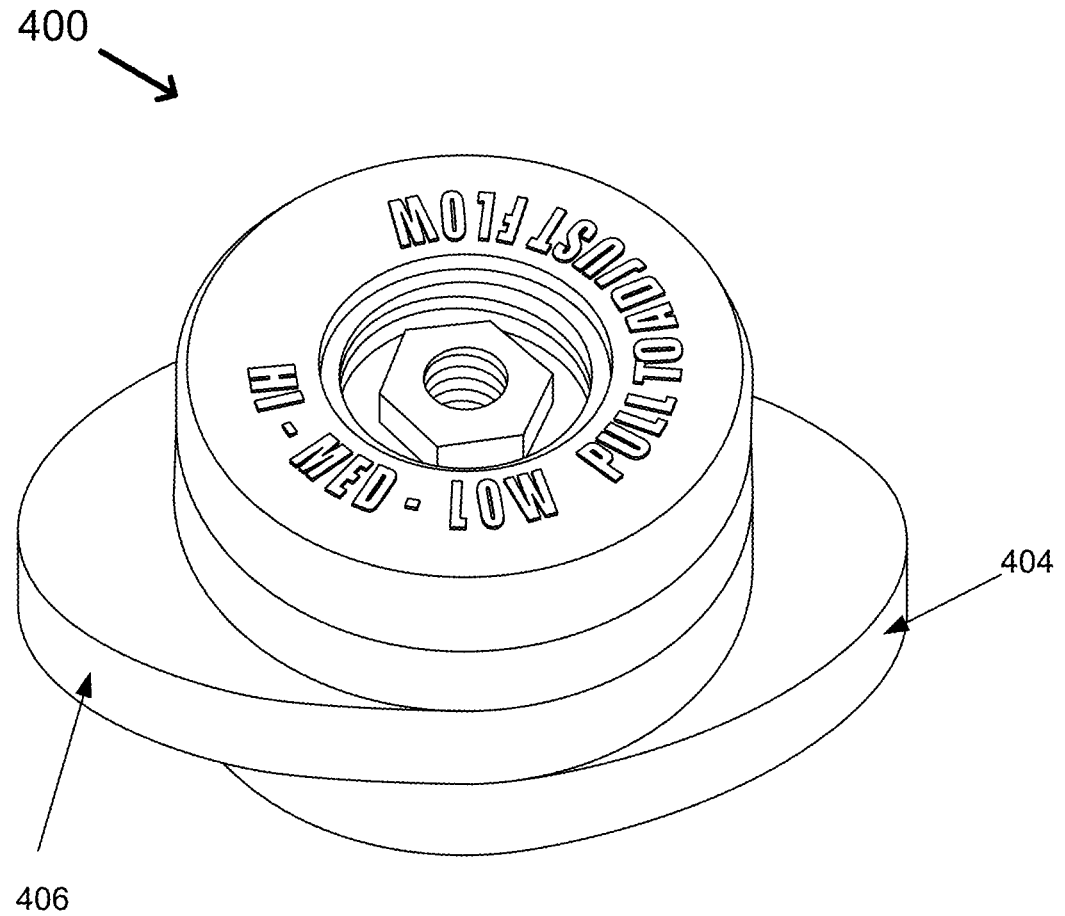
FIG. 4 illustrates a perspective view of a mechanically adjustable dual plane variable cam in fully extended orientation.
Figure 5F:
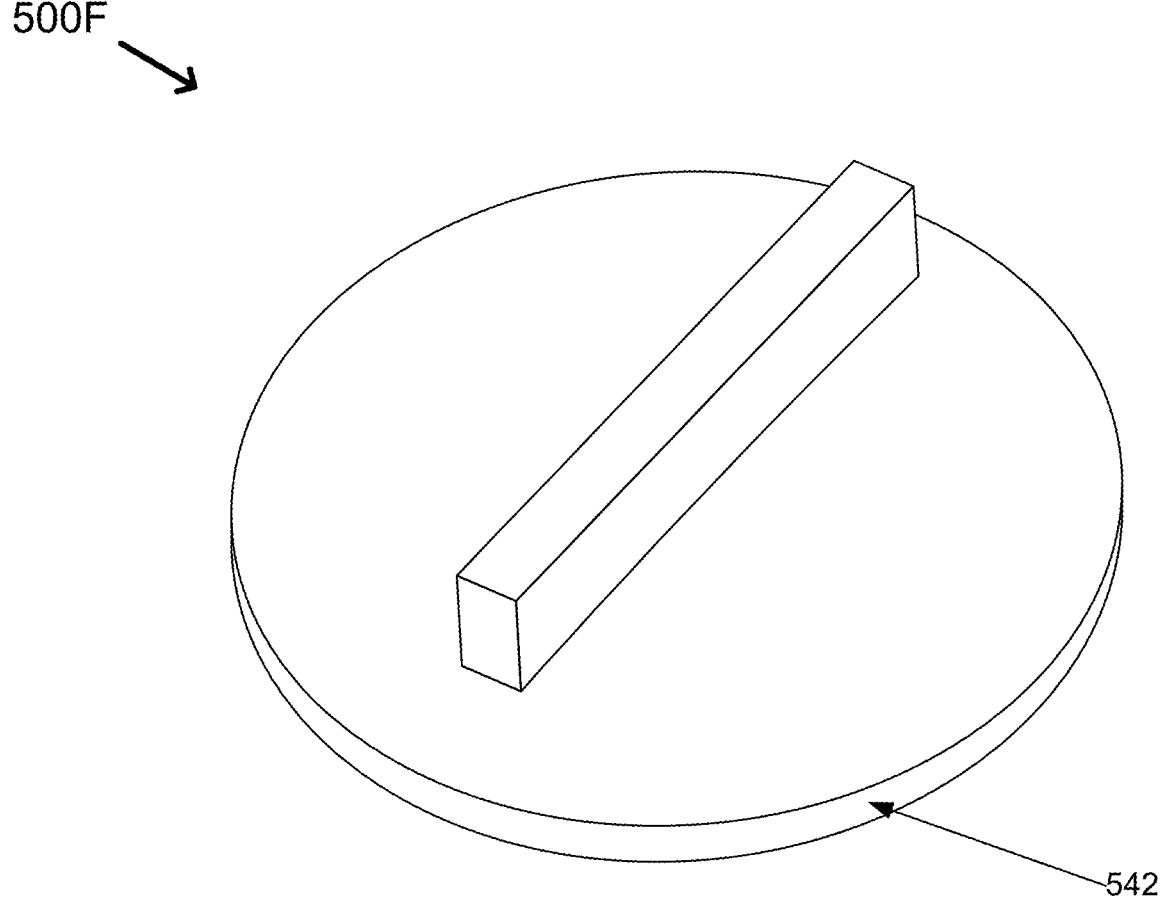
Figure 6A:
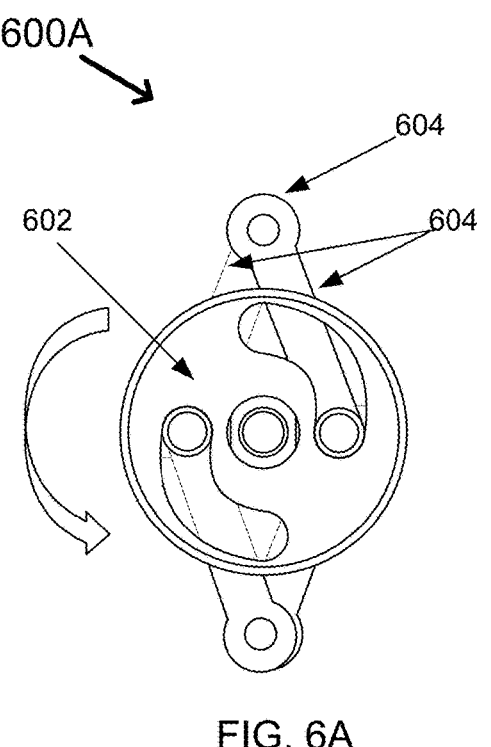
FIG. 6A through 6D illustrate views of a mechanically adjustable single plane variable cam in different operation states.
Figure 6B:
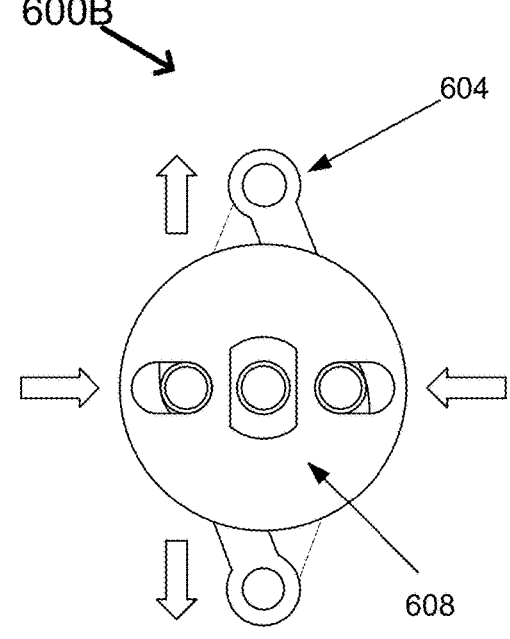
Figure 6C:
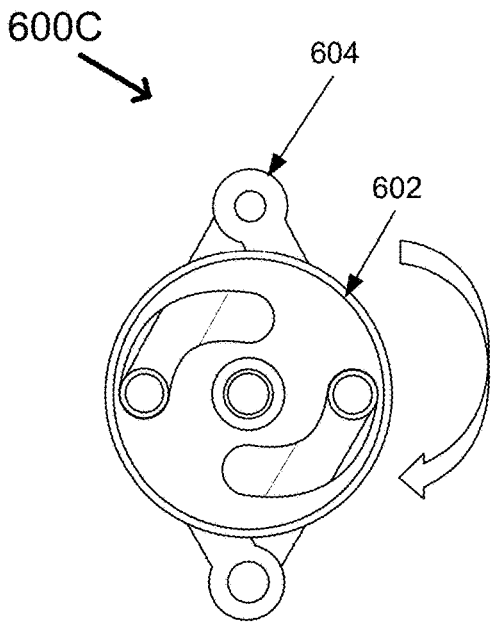
Figure 6D:
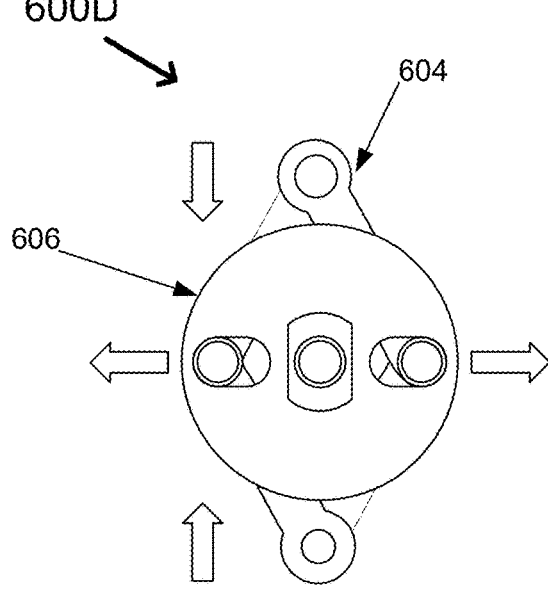

FIG. 4 illustrates a perspective view of a mechanically adjustable dual plane variable cam in fully extended orientation, arranged in accordance with at least some embodiments described herein.

By modifying the compressing arms to a multiple plane actuation (high and low) and placing the cam lobes on stacked vertical planes 404, 406 as shown in diagram 400, the compressor arms will only be actuated once per revolution, and therefore the motor can run at 2×shaft speed for the same actuation cycle. While this can be accomplished by adding spacers above or below the cam end, it may also be accomplished with a different configuration, where two individual cams arranged on multiple planes are driven from a central drive and have their location adjusted by the use of a scroll plate.

The example embodiment shown in diagram 400 also uses definitive locations on the scroll plate for volume adjustment, unlike the infinite adjustment of the single plane variable cam.

FIG. 5A through 5F illustrate various perspective views of individual components and partially assembled single plate cams, arranged in accordance with at least some embodiments described herein.

Diagram 500A shows a drive plate of a variable cam with radial drive slots 502, center shaft 504, internal thread 506 for locking in position, and driven shaft set screw 508. Diagram 500B shows a parallelogram arm assembly with polar arms 512, roller extensions 516, and working end 514. Diagram 500C shows a parallelogram arm assembly on a drive plate with the roller extensions 516 in drive slots. Diagram 500D shows a scroll plate with a shaft clearance hole 522 and scroll slots 524. Diagram 500E shows a scroll plate 532 installed on a variable cam assembly with the roller extensions 516 in scroll slots. Diagram 500F shows a lock cover 542 that includes a threaded stud on the underside (not shown) that matches the internal thread 506 on the drive plate. When the lock cover is tightened, the entire assembly may be locked in place due to compression and friction.

In a single plane embodiment, the example apparatus includes a drive plate (500A) that is affixed to the shaft of the driving motor. The drive plate has a central shaft around which the remainder of the components revolves. The drive plate also includes a number of radially aligned slots that only allow the parallelogram arms (500B) to move in a manner that increases or decreases the distance from center, while forcing the parallelogram arms to rotate around the axis.

The parallelogram arm assembly (500A) is arranged in a polar layout. All 4 arms may be identical in length and outline. There are 4 symmetrical pivot points which join the arms together. At the points where the arms fit into the drive plate (500A) or scroll plate (500D), there are roller extensions 516, which sit above and below the arms themselves. The roller extensions 516 drive the assembly from the drive plate (500A) side as well as determine the extension from the scroll plate side (500C).

The work side of the parallelogram arms 512 may or may not have additional rollers (not shown) on their ends, depending on intended usage. The parallelogram arms 512 can only move in one dimension, constrained by the slots in the drive plate (500A). The scroll plate (500D) has two "S" shaped slots that fit around the upper roller extensions on the parallelogram arm assembly (500B). The central hole 522 fits around the central shaft 504 on the drive plate (500A) which sets the axis of rotation. The central hole 522 allows the scroll plate (500D) to be tightened into the drive plate (500A) by the lock cover 542, which compresses the parallelogram arms 512 and holds them in position by tension and friction. As the scroll plate (500D) rotates, it pulls/pushes the parallelogram arm assembly (500B) wider/narrower in the restraint of the slots 502 in the drive plate which results in the work side 514 of the arms being nearer or further from the center of rotation, making the cam essentially longer or shorter in length.

The threaded stud end of the lock cover 542 is screwed into the internally threaded center shaft on the drive plate (500A). Once tightened down, the parallelogram arms 512 are no longer free to move about their axis.

FIG. 6A through 6D illustrate views of a mechanically adjustable single plane variable cam in different operation states, arranged in accordance with at least some embodiments described herein.

Diagram 600A shows scroll plate side of a variable cam in maximum extended position with scroll plate 602 secured through the center shaft and working ends 604, where the arms 606 are joined. Diagram 600B shows the drive plate side of the variable cam in maximum extended position with the drive plate 608 and working ends 604 extended beyond the drive plate 606. Diagram 600C shows scroll plate side of the variable cam in minimum extended position with scroll plate 602 and working ends 604. Diagram 600D shows the drive plate side of the variable cam in minimum extended position with the drive plate 606 and working ends 604.

To adjust the variable cam, the lock cover is loosened (does not have to be removed), and the scroll plate 602 is rotated either clockwise or counter-clockwise to increase or decrease the overall length of the cam, and therefore increasing or decreasing the volume of air introduced during a cycle. Diagrams 600B and 600D show maximum and minimum extensions and the cam can be locked into any desired intermediate position. The lock cover is then tightened against the drive plate 606, compressing and locking the assembly in position. The cam width is multiplied by the lever fulcrum of the pivot point, allowing relatively small changes to be amplified at the far end of the bag compression arms.

Figure 7A:
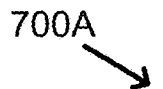
FIG. 7A illustrates a cutaway view of a dual plane variable cam.
Figure 7A:
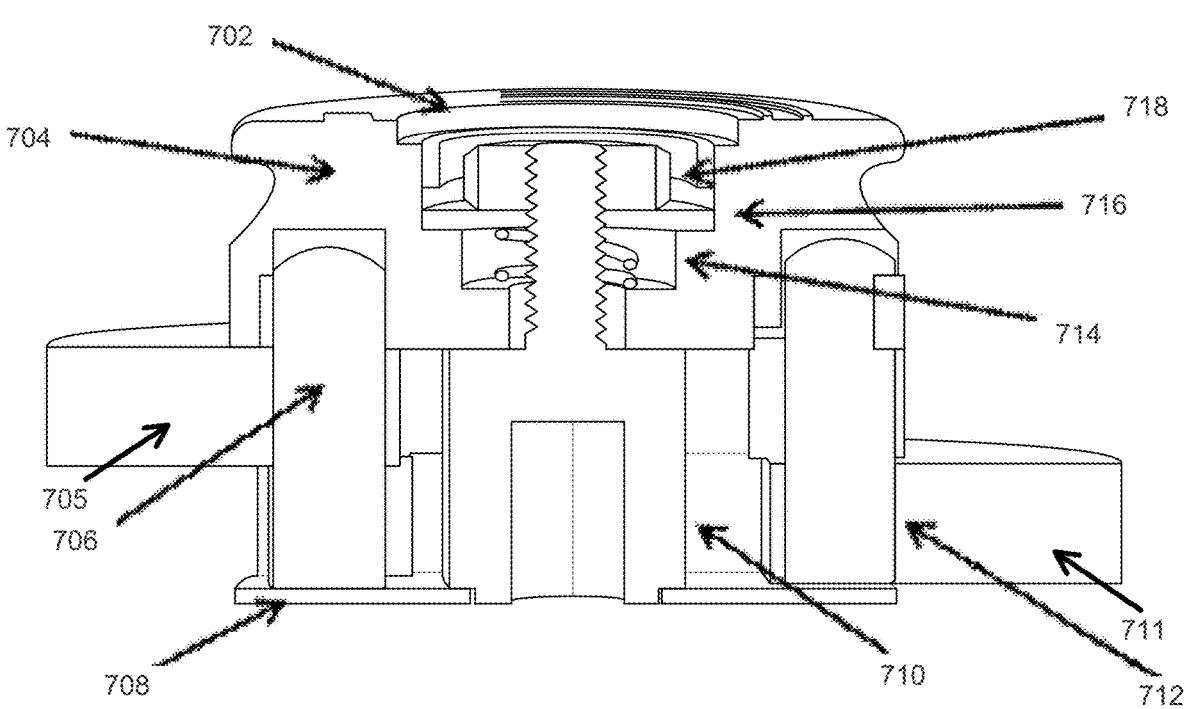

FIG. 7A illustrates a cutaway view of a dual plane variable cam, arranged in accordance with at least some embodiments described herein.

Diagram 700A shows the example dual plane variable cam with scroll block 704, which has an opening for cover plate 702 to fit in, fastening nut 718, circular spring 714, flat washer 716 with location indicator, base washer 708, drive block 710, and half drive cams 705, 711 with insert studs 706 and 712.

In a vertical order, the base washer is at the bottom of the assembly along with a bottom portion of the drive block 710. Half drive cams 705, 711 with the studs 706, 712 are lined up around the drive block, followed by the scroll block 704. The flat washer 716 and fastening nut 718 secure the scroll block 704 to the drive block 710 with the cover plate 702 fitting into a circular hole at the top of the scroll block 704.

Figure 7B:
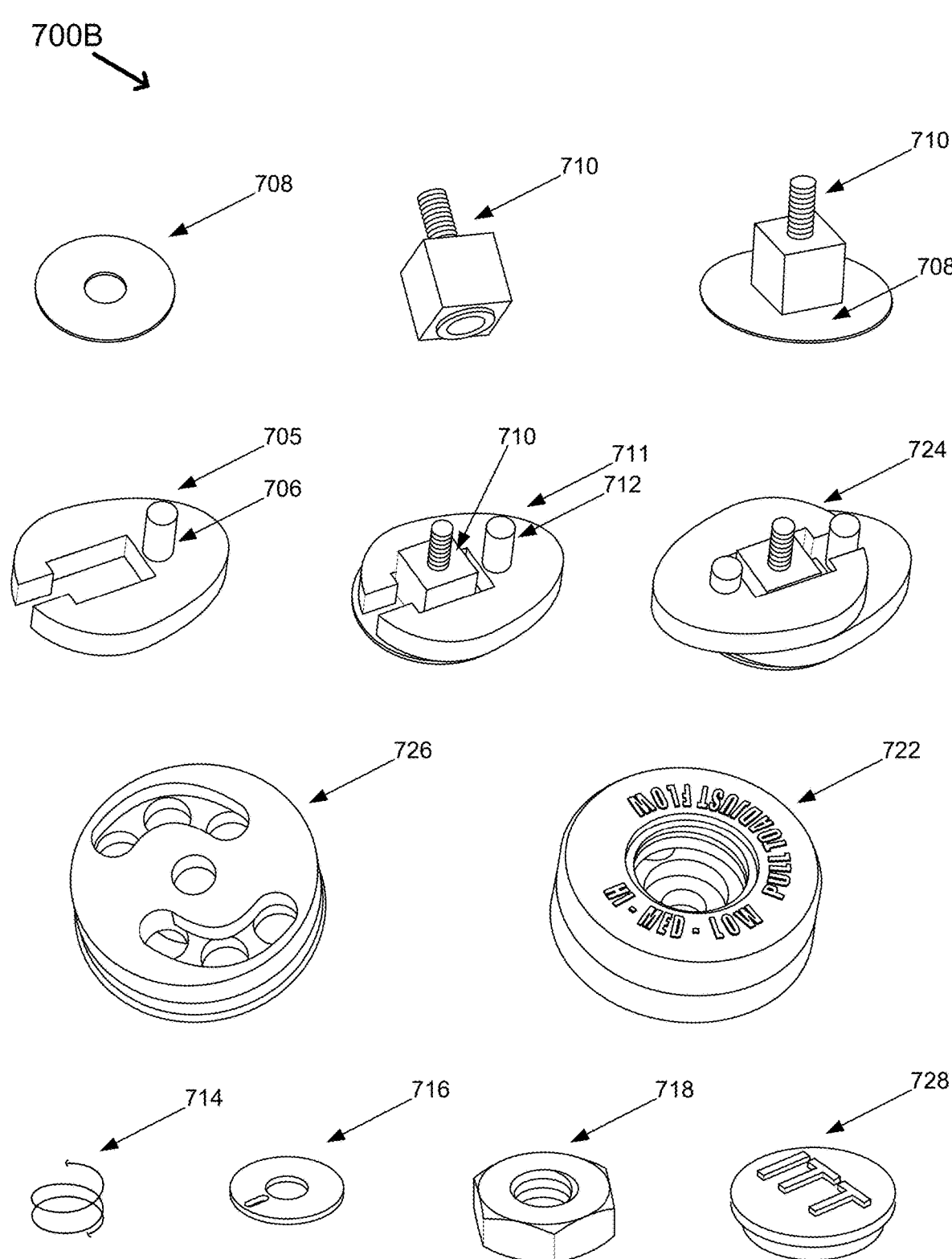
FIG. 7B illustrates perspective views of components of the dual plane variable cam of FIG. 7A.

FIG. 7B illustrates perspective views of components of the dual plane variable cam of FIG. 7A, arranged in accordance with at least some embodiments described herein.

Diagram 700B shows base washer 708 configured to restrain the cams in vertical direction, drive block 710, which attaches to motor shaft and maintains parallel arrangement of cams and limits size. The drive block 710 also has a threaded boss for scroll plate retention. Diagram 700B also includes half drive cam 705 with insert stud 706. The slot defines the movement around the drive block 710. In a dual plane variable cam, two identical half drive cams may be used. Diagram 700B shows drive block 710 aligned on base washer 708, half drive cam 711 assembled with the drive block (710) and both half drive cams 705, 711 assembled with the drive block (724). In the assembly 724, the half drive cams are identical in shape, but have different stud heights. The slot in the half drive cam 705 allows only parallel movement along square edge of drive block 710. The cutout in the edge of the half drive cam 711 allows for more movement. The half drive cam movements are restrained to a straight line along the slots.

Diagram 700B further shows top view 722 and bottom view 726 of the scroll block 704. The scroll block may be inserted similar to FIG. 5A, but with the addition of distinct recesses for the studs. The recesses lock the studs in place when the spring 714 forces the scroll block against the cam assembly. Diagram 700B also includes spring 714, flat washer with location indicator 716 to hold the assembly in place vertically, nut 718 to secure the scroll block 704 to the drive block 710, and cover plate 728. In some examples, the cover plate 728 may be clear so the position can be determined through the location indicator on the flat washer 716.

Figure 8:
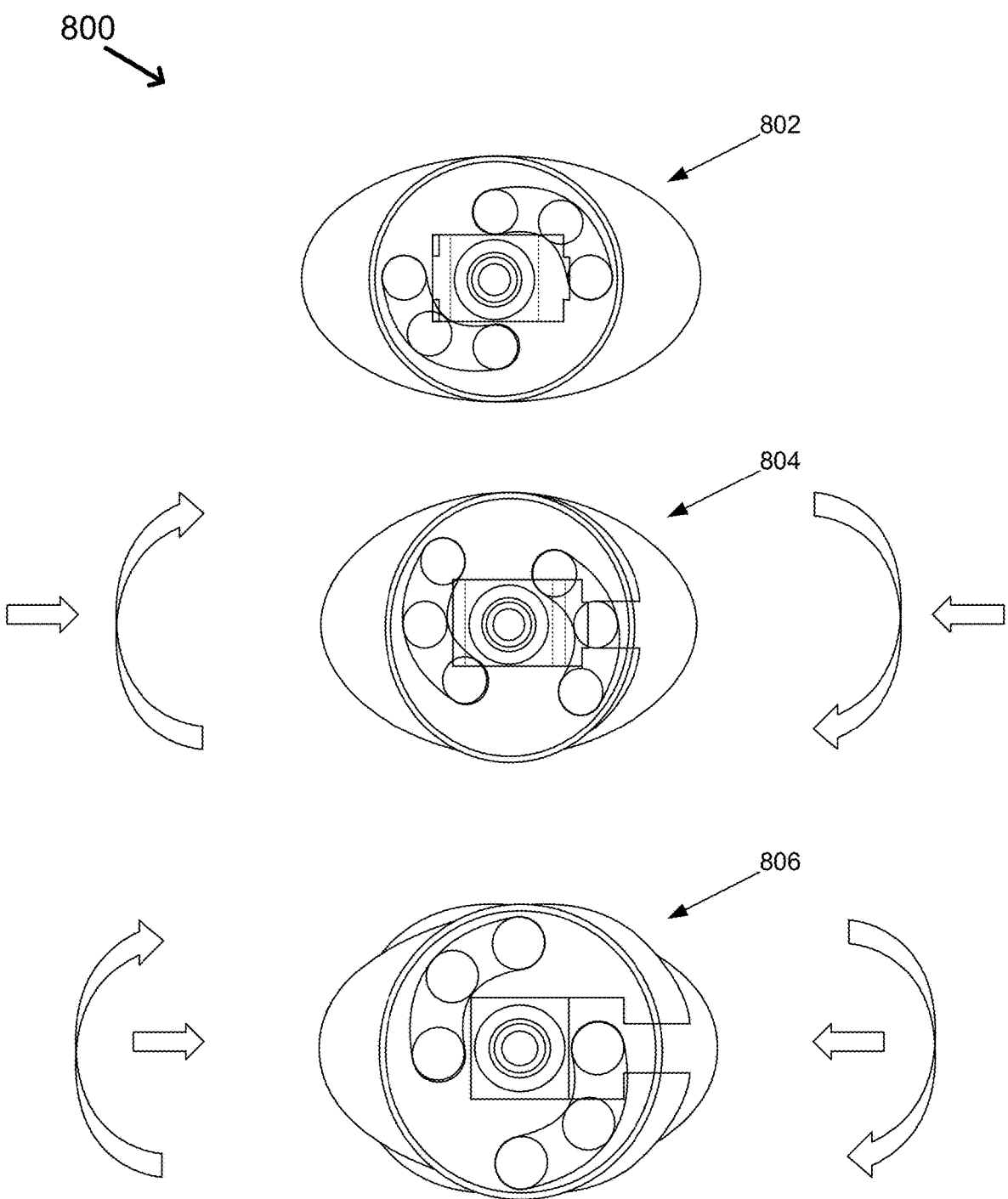
FIG. 8 illustrates views of a mechanically adjustable dual plane variable cam in different operation states, arranged in accordance with at least some embodiments described herein.

FIG. 8 illustrates views of a mechanically adjustable dual plane variable cam in different operation states, arranged in accordance with at least some embodiments described herein.

Diagram 800 shows a dual plane variable cam in full extension (802), the dual plane variable cam in medium extension rotated one position in clockwise direction (804), and the dual plane variable cam in minimum extension rotated one more position in clockwise direction (806).

To adjust the dual plane variable cam, the scroll plate is lifted to release the stud from the scroll recess, and the scroll plate is rotated either clockwise or counter-clockwise to increase or decrease the overall length of the cam by moving the half drive cams by their insert studs in the "S" shaped scroll cutouts closer or further apart, thereby increasing or decreasing the volume of air introduced during a cycle.

In diagram 800, maximum, intermediate, and minimum extensions are shown. The number of intermediate positions possible is determined by the overall size of the cams/slots and the diameter of the insert pins. The scroll plate is then indexed into one of the stud recesses against the insert studs, thereby locking the assembly in position. The cam width is multiplied by the lever fulcrum of the pivot point, allowing relatively small changes to be amplified at the far end of the bag compression arms.

The variable cam assembly can be made from a variety of materials, both metal and non-metals, primarily dependent on the load force or rotational speed of the device. The variable cam assembly can also be made up of a hybrid of materials. Pivot points can also be bushed or bearing surfaces, again dependent on expected usage. Springs can be coils, leaves or Bellville washers as appropriate. The drive plate can also be locked against the driving shaft in a variety of ways, set screws, press fit, or similar systems compatible with the materials being used and the force developed by the assembly.

According to some examples, a single plane variable camshaft may include a drive plate comprising a first substantially circular plate member, a center shaft member protruding from a center of the first circular plate member, where the first circular plate member defines two radial drive slots on opposing sides of the center shaft member; four arms movably coupled at respective endpoints and arranged in a polar configuration; four roller extensions coupled to respective end points of two pairs of the arms, where one pair of the roller extensions are arranged to fit into respective radial drive slots; and a scroll plate comprising a second substantially circular plate member. The second substantially circular plate member defines a substantially circular center hole to fit around the center shaft member and two "S" shaped scroll slots on opposing sides of the center hole, and another pair of the roller extensions are arranged to fit into respective scroll slots.

According to other examples, the radial drive slots are configured to allow the arms to move in a manner that increases or decreases their distance from a center of the drive plate while forcing the arms to rotate around the center. The distance is increased or decreased from the center of the drive plate through loosening of the lock cover and rotation of the scroll plate clockwise or counterclockwise. The arms are substantially equal in length. A top portion of the center shaft member is hollow and an inside surface of the top portion of the center shaft member is threaded. The camshaft may also include a lock cover comprising a cover member and a threaded stud, wherein the threaded stud is arranged to fit into the threaded top portion of the center shaft member. The lock cover, when tightened to the top portion of the center shaft member, is arranged to lock the camshaft in place.

According to further examples, a dual plane variable camshaft may include a base washer; a drive block aligned centrally with the base washer; a first half drive camshaft comprising a first camshaft member and a first stud that protrudes transversally from the first camshaft member, where the first camshaft member defines a substantially centrally located first opening to fit around the drive block; a second half drive camshaft comprising a second camshaft member and a second stud that protrudes transversally from the second camshaft member, where the second camshaft member defines a substantially centrally located second opening to fit around the drive block and a third opening to fit around the first stud; a substantially circular scroll block that defines a substantially circular center hole to fit around a threaded top portion of the drive block and two "S" shaped scroll slots on opposing sides of the center hole; a fastening mechanism to secure the transversally ordered base washer, drive block, first half drive camshaft, second half drive camshaft, and scroll block together, where the fastening mechanism is arranged to thread to the threaded top portion of the drive block; and a cover plate to fit into a substantially circular opening at a top surface of the scroll block.

According to yet other examples, the fastening mechanism includes a spring and a nut, the spring configured to force the scroll block toward the first and second half drive camshafts. The drive block includes a threaded boss for scroll plate retention. A size and shape of the first camshaft member and the second camshaft member are substantially similar, and the first stud and the second stud have different heights. The fastening mechanism further includes a washer with a location indicator, and a central portion of the cover plate is transparent to allow determination of camshaft position. The block drive is arranged to couple to a motor and receive rotational motion from the motor.

According to other examples, a bag mask valve (BMV) based resuscitator may include an inflatable bag arranged to provide air to a patient through a face mask or an endotracheal tube in response to compression/retraction actions applied to the inflatable bag; a motor; a pair of levers positioned to surround a central portion of the inflatable bag and arranged to provide the compression/retraction actions to the inflatable bag in response to a rotational motion from the motor; and a camshaft mechanically coupled between the motor and the pair of levers. The camshaft may include a drive plate comprising a first substantially circular plate member, a center shaft member protruding from a center of the first circular plate member, where the first circular plate member defines two radial drive slots on opposing sides of the center shaft member; four arms movably coupled at respective endpoints and arranged in a polar configuration; four roller extensions coupled to respective end points of two pairs of the arms, where one pair of the roller extensions are arranged to fit into respective radial drive slots; and a scroll plate comprising a second substantially circular plate member. The second substantially circular plate member defines a substantially circular center hole to fit around the center shaft member and two "S" shaped scroll slots on opposing sides of the center hole, and another pair of the roller extensions are arranged to fit into respective scroll slots.

According to some examples, the radial drive slots are configured to allow the arms to move in a manner that increases or decreases their distance from a center of the drive plate while forcing the arms to rotate around the center. The distance is increased or decreased from the center of the drive plate through loosening of the lock cover and rotation of the scroll plate clockwise or counterclockwise. The arms are substantially equal in length. The fastening mechanism includes a washer with a location indicator, and a central portion of the cover plate is transparent to allow determination of camshaft position.

According to further examples, a bag mask valve (BMV) based resuscitator may include an inflatable bag arranged to provide air to a patient through a face mask or an endotracheal tube in response to compression/retraction actions applied to the inflatable bag; a motor; a pair of levers positioned to surround a central portion of the inflatable bag and arranged to provide the compression/retraction actions to the inflatable bag in response to a rotational motion from the motor; and a camshaft mechanically coupled between the motor and the pair of levers. The camshaft may include a base washer; a drive block aligned centrally with the base washer; a first half drive camshaft comprising a first camshaft member and a first stud that protrudes transversally from the first camshaft member, where the first camshaft member defines a substantially centrally located first opening to fit around the drive block; a second half drive camshaft comprising a second camshaft member and a second stud that protrudes transversally from the second camshaft member, where the second camshaft member defines a substantially centrally located second opening to fit around the drive block and a third opening to fit around the first stud; a substantially circular scroll block that defines a substantially circular center hole to fit around a threaded top portion of the drive block and two "S" shaped scroll slots on opposing sides of the center hole; a fastening mechanism to secure the transversally ordered base washer, drive block, first half drive camshaft, second half drive camshaft, and scroll block together, where the fastening mechanism is arranged to thread to the threaded top portion of the drive block; and a cover plate to fit into a substantially circular opening at a top surface of the scroll block. According to some examples, a distance of the arms from a center of the drive plate is adjustable and determines a volume of air introduced during a compression/retraction cycle.

The present disclosure is not to be limited in terms of the particular embodiments described in this application, which are intended as illustrations of various aspects. Many modifications and variations can be made without departing from its spirit and scope. Functionally equivalent methods and apparatuses within the scope of the disclosure, in addition to those enumerated herein, are possible from the foregoing descriptions. Such modifications and variations are intended to fall within the scope of the appended claims. The present disclosure is to be limited only by the terms of the appended claims, along with the full scope of equivalents to which such claims are entitled. The terminology used herein is for the purpose of describing particular embodiments only and is not intended to be limiting.

The herein described subject matter sometimes illustrates different components contained within, or connected with, different other components. Such depicted architectures are merely examples, and in fact, many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically connectable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

For any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments are possible. The various aspects and embodiments disclosed herein are for purposes of illustration and are not intended to be limiting, with the true scope and spirit being indicated by the following claims.

What is claimed is:

1. A single plane variable camshaft comprising:
a drive plate comprising a first substantially circular plate member, a center shaft member protruding from a center of the first substantially circular plate member, wherein the first substantially circular plate member, defines two radial drive slots on opposing sides of the center shaft member;

four arms movably coupled at respective endpoints and arranged in a polar configuration;

four roller extensions coupled to the respective endpoints of two pairs of the arms, wherein one pair of the roller extensions are arranged to fit into respective radial drive slots of the two radial drive slots; and a scroll plate comprising a second substantially circular plate member, wherein the second substantially circular plate member defines a substantially circular center hole to fit around the center shaft member and two arc shaped scroll slots on opposing sides of the center hole, and another pair of the roller extensions are arranged to fit into respective arc shaped scroll slots of the two arc shaped scroll slots.

2. The camshaft of claim 1, wherein the radial drive slots are configured to allow the arms to move in a manner that increases or decreases a distance from a center of the drive plate while forcing the arms to rotate around the center of the drive plate.

3. The camshaft of claim 2, wherein the distance is increased or decreased from the center of the drive plate through loosening of a lock cover and rotation of the scroll plate clockwise or counterclockwise.

4. The camshaft of claim 1, wherein the arms are substantially equal in length.

5. The camshaft of claim 1, wherein a top portion of the center shaft member is hollow and an inside surface of the top portion of the center shaft member is threaded.

6. The camshaft of claim 5, further comprising:

a lock cover comprising a cover member and a threaded stud, wherein the threaded stud is arranged to fit into the threaded top portion of the center shaft member.

7. The camshaft of claim 6, wherein the lock cover, when tightened to the top portion of the center shaft member, is arranged to lock the camshaft in place.

8. A bag mask valve (BMV) based resuscitator comprising:

an inflatable bag arranged to provide air to a patient through a face mask or an endotracheal tube in response to compression and/or retraction actions applied to the inflatable bag;

14 a motor;

a pair of levers positioned to surround a central portion of the inflatable bag and arranged to provide the compression and/or retraction actions to the inflatable bag in response to a rotational motion from the motor; and a camshaft mechanically coupled between the motor and the pair of levers, the camshaft comprising:

a drive plate comprising a first substantially circular plate member, a center shaft member protruding from a center of the first substantially circular plate member, wherein the first substantially circular plate member defines two radial drive slots on opposing sides of the center shaft member;

four arms movably coupled at the respective endpoints and arranged in a polar configuration;

four roller extensions coupled to respective end points of two pairs of the arms, wherein one pair of the roller extensions are arranged to fit into respective radial drive slots of the two radial drive slots; and a scroll plate comprising a second substantially circular plate member, wherein the second substantially circular plate member defines a substantially circular center hole to fit around the center shaft member and two arc shaped scroll slots on opposing sides of the center hole, and another pair of the roller extensions are arranged to fit into respective arc shaped scroll slots of the two arc shaped scroll slots.

9. The resuscitator of claim 8, wherein the radial drive slots are configured to allow the arms to move in a manner that increases or decreases a distance from a center of the drive plate while forcing the arms to rotate around the center of the drive plate.

10. The resuscitator of claim 9, wherein the distance is increased or decreased from the center of the drive plate through loosening of a lock cover and rotation of the scroll plate clockwise or counterclockwise.

11. The resuscitator of claim 8, wherein the arms are substantially equal in length.

12. The resuscitator of claim 8, wherein a fastening mechanism includes a washer with a location indicator, and a central portion of a cover plate is transparent to allow for a position of the camshaft to be determined.

* * * * *